United States Patent [19]

Vogt et al.

[11] 4,018,708
[45] Apr. 19, 1977

[54] TIN-TITANIUM COMPLEXES AS ESTERIFICATION/TRANSESTERIFICATION CATALYSTS

[75] Inventors: Herwart C. Vogt, Grosse Ile; Manher Parekh, Woodhaven; John T. Patton, Jr., Wyandotte, all of Mich.

[73] Assignee: BASF Wyandotte Corporation, Wyandotte, Mich.

[22] Filed: Dec. 29, 1975

[21] Appl. No.: 644,358

[52] U.S. Cl. .................. 252/431 C; 252/431 R
[51] Int. Cl.² .................................. B01J 31/12
[58] Field of Search .............. 252/431 C, 431 R

[56] References Cited

UNITED STATES PATENTS

| | | | |
|---|---|---|---|
| 3,056,818 | 10/1962 | Werber | 252/431 C |
| 3,714,234 | 1/1973 | White | 252/431 R |
| 3,716,523 | 2/1973 | Cook | 260/75 M |
| 3,884,832 | 5/1975 | Pullukat et al. | 252/431 R |

Primary Examiner—Winston A. Douglas
Assistant Examiner—John F. Niebling
Attorney, Agent, or Firm—Norbert M. Lisicki; Bernhard R. Swick; Robert E. Dunn

[57] ABSTRACT

Complexes of quadrivalent organotin and quadrivalent organotitanium compounds are effective esterification and transesterification catalysts.

8 Claims, No Drawings

TIN-TITANIUM COMPLEXES AS ESTERIFICATION/TRANSESTERIFICATION CATALYSTS

BACKGROUND OF THE INVENTION

1. Field of the Invention

This invention relates to the preparation of quadrivalent organotin and quadrivalent organotitanium complexes. More specifically, this invention relates to a process of preparing esters and polyesters in an improved manner by using these novel complexes as esterification/transesterification catalysts.

2. Prior Art

The preparation of esters and polyesters is well known in the art. These materials are prepared by esterifying mono- and/or polyhydric alcohols with mono- and/or polycarboxylic acids. In many instances it is desirable to prepare such esters or polyesters having a very low acid number, i.e., less than two. However, the attainment of an ester or polyester having a low acid number is extremely difficult to achieve. For example, during the last stage of the esterification of the reaction, the reaction proceeds extremely slowly and hence in order to reduce the acid value it is necessary to heat for a lengthy period of time at relatively high temperatures. This, in many instances, tends to bring about formation of a darkened ester or polyester which is unsuitable for further use. Various attempts have been made to reduce the time of the esterification reaction. For instance, British Patent No. 792,011 describes the use of iron, cadmium, cobalt, lead, zinc, antimony and manganese in the form of the metal, its oxide or its salt with a dibasic acid. Other catalyst types are more reactive. For example, stannous compounds of the type $Sn(OOCR)_2$ wherein R is selected from the group consisting of saturated and unsaturated aliphatic hydrocarbon constituents having from about 7 to about 17 carbon atoms have been described in U.S. Pat. No. 3,162,616 and U.S. Pat. No. 3,716,523. Organo titanium or organo zirconium compounds have been disclosed by U.S. Pat. No. 3,056,818 as being suitable as esterification catalysts. Titanium compounds are often insoluble in the product and must be removed by filtration or other tedious procedures. The technical literature also notes that esterification is usually effected by refluxing the acid and alcohol with a small amount of acid catalyst such as sulfuric acid, hydrochloric acid, and sulfonic acids or boron trifluoride. Acid catalyst often causes side reactions and color formation and must be removed to insure a stable low acid number product.

Esters may also be prepared by transesterification reactions. These transesterification reactions include the reactions between two esters to yield two new esters or the reaction between an ester and an alcohol to form a new ester and liberate an alcohol. Included also are the transesterification reactions where the components of the esters involved are polyhydroxy alcohols and polybasic acids. These reactions may, in some instances, be catalyzed by those substances which are employed for the esterification procedure. We have discovered that polyesters having an acid number less than two can be prepared in relatively short periods of time employing either esterification or transesterification procedures with quadrivalent organotin and quadrivalent organotitanium complexes as catalysts.

SUMMARY OF THE INVENTION

It has been discovered that certain unique combinations between quadrivalent organotin and quadrivalent organotitanium compounds will result in esterification/transesterification catalysts which are more efficient than the individual metal compounds themselves. The complexes may be used for any type of mono- or polycarboxylic acid and anhydride to be esterified with any suitable hydroxyl containing material.

DESCRIPTION OF THE PREFERRED EMBODIMENTS

The tin-titanium complexes may be described by the following formula:

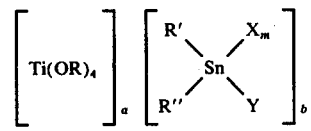

wherein R is a radical selected from the group consisting of an aliphatic radical having from 1 to 18 carbon atoms, an alicyclic radical having between 1 and 3 rings, between 5 and 6 carbon atoms per ring and between 5 and 18 carbon atoms per molecule; and an aromatic radical having between 1 and 3 rings and between 6 and 18 carbon atoms per molecule, R' and R'' are individually alkyl, aryl, alicyclic groups containing 1 to 18 carbon atoms and may be the same or different, X is an alkyl, aryl, alicyclic, heterocyclic, alkoxyl, or carboxyl group having 1 to 18 carbon atoms, Y is an alkoxy or carboxyl group each containing from 1 to 18 carbon atoms, an oxy or ether group or a group represented by the following formula:

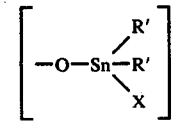

provided that when Y is this group, X is an alkyl group, m is equal to 1 except when Y is an oxy group then m is equal to 0, and a and b are whole numbers in the ratio of 1:1 to 1:4 and preferably 1:1 to 1:2.

The tin-titanium complexes of this invention are prepared by reacting together, under anhydrous conditions, and in the absence of air, at room temperature or elevated temperatures, the desired concentration of quadrivalent organotin compound with the desired amount of quadrivalent organotitanium compound. It may also be desired to heat the reactants if shorter reaction times are desired and to assure completeness of reaction. The reaction of these two clear liquids is often accompanied by orange, or light yellow color formation and the liberation of heat. Sometimes it is desirable to carry out this preparation in a suitable inert solvent to permit easier handling of the catalyst. Solvents such as anhydrous xylene may be employed. In addition to the color formation and heat evolution which indicate a new complex compound has been formed, it has been found that the tin-titanium complex has improved hydrolytic stability. It is well known that quadrivalent organotin and quadrivalent organotitanium compounds are very susceptible to trace amounts of moisture which leads to rapid hydrolysis, catalyst deactivation, and often solid formation. For example, tetrabutyl titanate is immediately decomposed by water forming titanic acid. Atmospheric moisture may produce high molecular weight condensation products which proceed until titanium dioxide or the hydrous titanium dioxide is formed. Dibutyltin diacetate undergoes similar hydrolysis type reactions with water and precautions must be taken to prevent the destruction of the catalyst.

Those quadrivalent organotin compounds which are used to prepare the catalyst complex, as described in the formula above, are dibutyltin dilaurate, dibutyltin diacetate, dibutyltin di(2-ethylhexoate), dioctyltin dilaurate, dibutyltin maleate, di(n-octyl)tin maleate, bis(dibutyl acetoxy tin) oxide, bis(dibutyl lauroxyloxy tin) oxide, dibutyltin dibutoxide, dibutyltin dimethoxide, dibutyltin disalicylate, dibutyltin bis(isooctyl maleate), dibtuyltin bis(isopropyl maleate), dibutyltin oxide, tributyltin acetate, tributyltin isopropyl succinate, tributyltin linoleate, tributyltin nicotinate, dimethyltin dilaurate, dimethyltin oxide, dioctyltin oxide, bis(tributyltin) oxide, diphenyltin oxide, triphenyltin acetate, tri-n-propyltin acetate, tri-n-propyltin laurate, and bis(tri-n-propyltin) oxide.

Those preferred are dibutyltin diacetate, dibutyltin dilaurate, dibutyltin di(2-ethylhexoate), dioctyltin dilaurate, and bis(tributyltin) oxide. Mixtures of any of the above may be employed.

The quadrivalent organotitanium compounds which can be employed include tetramethyl titanate, tetraethyl titanate, tetrallyl titanate, tetrapropyl titanate, tetraisopropyl titanate, tetrabutyl titantate, tetraisobutyl titanate, tetraamyl titanate, tetracyclopentyl titanate, tetrahexyl titanate, tetracyclohexyl titanate, tetrabenzyl titanate, tetraoctyl titanate, tetraethylhexyl titanate, tetranonyl titanate, tetradecyl titanate, and tetraoleyl titanate.

Mixed alkyl titanate compounds would include trimethylbutyl titanate, dimethyldibutyl titanate, triethylbutyl titanate, methyl isopropyl dibutyl titanate, diethyl dibutyl titanate, propyl tributyl titanate, ethyl tricyclohexyl titanate, diisopropyl dioctadecyl titanate, and dibutyl dioctadecyl titanate.

Included among the aromatic titanates are tetraphenyl titanate, o- and m-tetramethylphenyl titanate, and 1- and 2-tetranaphthyl titanate.

Mixtures of any of the above may be employed.

The concentrations of complex which may be employed as a catalyst in the preparation of ester of polyester polyols can be varied over a fairly wide range. Small amounts such as 0.000033 mole of catalyst (0.33 × 10$^{-4}$) per 1000 grams of ester or polyester have been successfully employed and amounts as high as 0.0264 mole of complex (264 × 10$^{-4}$) per 1000 grams of polymer or higher can be used. Preferably, amounts less than 0.0026 mole of complex per 1000 grams of ester or polyester (26.46 × 10$^{-4}$) are employed. The presence of large quantities may result in the presence of an unwanted impurity depending upon the future use of the ester of polyester polyol. The complex may be initially introduced with the material to be esterified, or it may be introduced at the time when the esterification reaction has slowed down and the acid number has reached a value of about 15–20. Reaction conditions under which esterification is effected can be varied considerably. The reaction generally proceeds very slowly at room temperature but at elevated temperatures, the reaction rate is quite rapid so that about 85–95 percent of the acid is converted to ester within a few hours. To force the equilibrium towards the formation of the product the water of esterification is removed as rapidly as it forms. One accepted way this can be accomplished is by carrying out the reaction in a liquid medium which forms an azeotrope with water having a boiling point that is lower than that of either component of the reaction. It is to be understood, however, that if the reactants and the esters which result, boil at temperatures well above 100° Centigrade at atmospheric pressure, the reaction temperature can be sufficiently high and would not require azeotrope forming liquid reaction medium. Generally, temperatures of 150°–240° Centigrade are employed. The reaction can be carried out under reduced or superimposed pressures. To facilitate water removal at the later stages of esterification, a vacuum of 0.1–100 mm Hg is employed. The time of reaction will depend on the reactivity of the reactants, the stoichiometry, temperature, and pressure employed in the reaction, the molecular weight of the resulting polyester, the rapidity with which the water of esterification is removed, and the activity of the catalyst employed, if any.

Any mono- or polycarboxylic acid and anhydrides thereof may be employed for the preparation of esters. Thus, the acids undergoing esterification can be aliphatic, cycloaliphatic or aromatic and they can be substituted or unsubstituted. Among the acids which may be employed include acetic, acrylic, propionic, propiolic, isobutyric, methacrylic, n-butyric, pivalic, ethylmethylacetic, isovaleric, chloroacetic, α-chloropropionic, n-valeric, dichloroacetic, diethylacetic, isocaproic, α-ethyl-n-butyric, methoxyacetic, n-caproic, ethoxyacetic, bromoacetic, heptoic, α-ethyl-n-caproic, β-bromoisovaleric, hexahydrobenzoic, dibromoacetic, n-caprylic, α-phenylpropionic, undecanoic, β-phenylpropionic, mesitylenic, tricarbally-lic, α,β-dibromosuccinic, tartaric, 3,5-dinitrosalicylic, p-toluic, acetylenedicarboxylic, veratric (anhydrous), p-fluorobenzoic, 2,4-dinitrobenzoic, anisic, β-naphthoic, acetylanthranilic, camphoric, hippuric, succinic, aconitic, m-nitrocinnamic, 2-chloro-3,5-dinitrobenzoic, fumaric, m-hydroxybenzoic, p-coumaric, phthalic, o-coumaric, p-hydroxybenzoic, β-resorcylic, tetrachlorophthalic, p-bromobenzoic, isophthalic, terephthalic, trimesic, β-benzoylpropionic, p-isopropylbenzoic, benzoic, o-benzoylbenzoic, γ-benzoylbutyric, 2,4-dimethylbenzoic, maleic, o-(p-toluyl)-benzoic, 2,5-dimethylbenzoic, sebacic, mandelic, cinnamic, acetylsalicylic, phenylpropiolic, glutaconic (cis), glutaconic (trans), 2,6-dichlorobenzoic, o-chlorobenzoic, m-nitrobenzoic, meso-tartaric, suberic, furylacrylic, o-nitrophenylacetic, 3-nitrosalicylic, diphenylacetic, o-nitrobenzoic, phthalonic, p-hydroxyphenylacetic, o-bromobenzoic, benzilic, adipic, p-nitrophenylacetic, 2,5-dichlorobenzoic, citric, m-bromobenzoic, 2,4,6-trimethylbenzoic, salicylic, m-chlorobenzoic, 2,4-dichlorobenzoic, α-naphthoic, 2,3-dichlorobenzoic, 3,4-dimethylbenzoic, oleic, methacrylic, lactic, β-bromoisobutyric, thiobenzoic, undecylenic, undecanoic, hexahydrobenzoic, capric, pivalic, β-chloropropionic, lauric, angelic, dibromoacetic, β-phenylpropionic (hydrocinnamic), α-bromoisobutyric, bromoacetic, elaidic, γ-phenylbutyric, myristic, trichloroacetic, β-bromopropionic, palmitic, chloroacetic, α,β-dibromopropionic, cyanoacetic, stearic, crotonic (trans), phenylacetic, glycolic, citranconic, phenoxyacetic, phthalaldehydic, glutaric, o-methoxybenzoic, o-toluic, pimelic, azelaic, m-toluic, ethylmalonic, malonic, suberic, brassylic, thapsic, fumaric, glutaconic, α-hydromuconic, β-hydromuconic, α-butyl-α-ethyl glutaric, α,β-ethyl succinic, isophthalic, terephthalic, hemimellitic, 1,4-cyclohexane dicarboxylic.

Anhydrides of mono- and polybasic acids can be used in place of the acids. These include acetic anhydride, propionic anhydride, n-butyric anhydride, citaconic anhydride, n-valeric anhydride, crotonic anhydride, n-heptoic anhydride, benzoic anhydride, chloroacetic anhydride, maleic anhydride, itaconic anhydride, 4-nitrophthalic anhydride, succinic anhydride, cinnamic anhydride, phthalic anhydride, 1,2-naphthalic anhydride, camphoric anhydride, 2,3-naphthalic anhydride, α-naphthoic anhydride, 1,8-naphthalic anhydride, tetrabromophthalic anhydride, and tetrachlorophthalic anhydride.

Amond the monohydric and polyhydric alcohols which can be reacted with carboxylic acids and anhydrides include methyl alcohol, ethyl alcohol, isopropyl alcohol, tertbutyl alcohol, allyl alcohol, n-propyl alcohol, sec-butyl alcohol, tert-amyl alcohol, isobutyl alcohol, methylisopropylcarbinol, n-butyl alcohol, diethylcarbinol, sec-amyl alcohol, ethylene monomethyl ether, 1-chloro-2-propanol, sec-butylcarbinol, ethylene chlorohydrin, isoamyl alcohol, 4-methyl-2-pentanol, 2-chloro-1-propanol, ethylene glycol monoethyl ether, 3-hexanol, methylisobutylcarbinol, n-amyl alcohol, cyclopentanol, 2-ethyl-1-butanol, 2-bromoethanol, di-n-propylcarbinol, n-hexyl alcohol, 2-heptanol, 2-methylcyclohexanol, furfuryl alcohol, ethylene glycol mono-n-butyl ether, 4-methylcyclohexanol, 3-methylcyclohexanol, cyclohexanol, trichloroethyl alcohol, lauryl alcohol, cinnamyl alcohol, α-terpineol, o-tolylcarbinol, myristyl alcohol, menthol, anisyl alcohol, pinacol hydrate, p-tolylcarbinol, sorbitol, triphenylcarbinol, mannitol, benzopinacol, borneol, inositol, pentaerythritol, diisobutylcarbinol, n-heptyl alcohol, tetrahydrofurfuryl alcohol, 2-octanol, cyclohexylcarbinol, 2,3-dichloro-1-propanol, 2-ethyl-1-hexanol, propylene glycol, n-octyl alcohol, diethylene glycol monomethyl ether, ethylene glycol, diethylene glycol monoethyl ether, methylphenylcarbinol, benzyl alcohol, n-nonyl alcohol, trimethylene glycol, m-tolycarbinol, β-phenylethyl alcohol, ethylphenylcarbinol, diethylene glycol mono-n-butyl ether, n-decyl alcohol, γ-phenylpropyl alcohol, diethylene glycol, ethylene glycol monophenyl ether, cinnamyl alcohol, glycerol, benzohydrol, dipropylene glycol, triethylene glycol, tetraethylene glycol, 1,4-tetramethylene glycol, 1,2-butylene glycol, 1,4-butanediol, 1,3-butanediol, 1,5-pentanediol, 1,4-pentanediol, 1,3-butanediol, 1,6-hexanediol, 1,7-heptanediol, 1,1,1-trimethylolpropane, 1,1,1-trimethylolethane, hexane-1,2,6-triol, neopentyl glycol, 1,10-decanediol, and 2,2 bis(4-hydroxycyclohexyl) propane.

The following Example are provided to further illustrate the invention. In these Examples the compounds designated by letters A, B, C, D, E, F, and G are as follows:

Compound A is dibutyltin dilaurate.
Compound B is dibutyltin diacetate.
Compound C is tetrabutyl titanate.
Compound D is tetraisopropyl titanate.
Compound E is dibutyltin di(2-ethylhexoate).
Compound F is dioctyltin dilaurate.
Compound G is bis(tributyltin) oxide.

The designations C/A, C/2A, D/2B, etc., indicate the relative mole ratios of the respective compounds employed to form the complexes. Parts and percents are by weight unless otherwise indicated.

EXAMPLE 1

In an insulated 50-milliliter round bottom flask equipped with a stirrer, thermometer, dropping funnel and a nitrogen sparge tube, 2.84 grams (0.01 mole) of tetraisopropyl titanate at a temperature of 25° Centigrade was carefully added with stirring to 12.60 grams (0.02 mole) of dibutyltin dilaurate at a temperature of 25° Centigrade. The temperature of the mixture rose to 30° Centigrade in 5 minutes with a simultaneous development of a deep orange-yellow color. The complex was stored in a dark brown glass bottle under nitrogen.

EXAMPLE 2

Into equipment similar to that of Example 1, 3.40 grams (0.01 mole) of tetrabutyl titanate at 25° Centigrade was added to 7.01 grams (0.02 mole) of dibutyltin diacetate at 25° Centigrade. The temperature of the mixture rose to 31° Centigrade with the formation of a light yellow color.

EXAMPLE 3

The compounds listed below were prepared in a manner similar to that of Example 1. Gardner color determinations were made of the resultant compounds. The resulting color formations shown below indicate that complex formation has occurred.

Table I

| Compound | Gardner Color |
| --- | --- |
| A | 1 |
| B | 1 |
| C | 2 |
| D | 1 |
| E | 1 |
| F | 2 |
| D/A | 13 |
| D/2A | 14 |
| D/3A | 11 |
| D/4A | 6 |
| C/2B | 3 |
| C/2A | 6 |
| C/2E | 3 |
| D/2F | 4 |

EXAMPLES 4–27

The Examples of Table II illustrate the hydrolytic stability of the tin-titanium complexes. The mole ratio of the quadrivalent organotin to quadrivalent organotitanium compound was varied as shown below. The water concentration was kept constant at $55 \times 10^{-4}$ moles. The indicated concentrations of each component were added to glass test tubes, stoppered and vigorously shaken. The solutions were then observed for any development of haze indicating hydrolysis had occurred.

Table II

| Example No. | Mole Ratio A:C | Moles of Compound A × $10^{-4}$ | Moles of Compound C × $10^{-4}$ | Appearance |
| --- | --- | --- | --- | --- |
| 4 | — | 50 | — | Hazy solution |
| 5 | — | — | 50 | White precipitate |
| 6 | 1:2 | 25 | 50 | Hazy solution |
| 7 | 1:1 | 50 | 50 | Clear solution |

Table II-continued

| Example No. | Mole Ratio A:C | Moles of Compound A × 10⁻⁴ | Moles of Compound C × 10⁻⁴ | Appearance |
|---|---|---|---|---|
| 8 | 2:1 | 50 | 25 | Clear solution |
| 9 | 4:1 | 50 | 12.5 | Hazy solution |
| 10 | 8:1 | 50 | 6.25 | Hazy solution |
| 11 | — | — | 50 | White precipitate |
| 12 | 1:2 | 25 | 50 | White precipitate |
| 13 | 1:1 | 50 | 50 | Clear solution |
| 14 | 2:1 | 50 | 25 | Clear solution |
| 15 | 4:1 | 50 | 12.5 | Hazy solution |
| 16 | 8:1 | 50 | 6.25 | Hazy solution |
| 17 | — | 50 | — | White precipitate |
| 18 | 1:2 | 50 | 100 | White precipitate |
| 19 | 1:1 | 50 | 50 | White precipitate |
| 20 | 2:1 | 50 | 25 | Clear solution |
| 21 | 4:1 | 50 | 12.5 | Hazy solution |
| 22 | 8:1 | 50 | 6.25 | White precipitate |
| 23 | 1:2 | 50 | 100 | White precipitate |
| 24 | 1:1 | 50 | 50 | Clear solution |
| 25 | 2:1 | 50 | 25 | Clear solution |
| 26 | 4:1 | 50 | 12.5 | Hazy solution |
| 27 | 8:1 | 50 | 6.25 | Hazy solution |

EXAMPLES 28–36

The polyester employed in the Examples below was prepared by the following procedure:

Into a 22-liter, four-neck, round bottom reaction vessel, equipped with stirrer, thermometer distillation head, glass helix packed column, condenser, vacuum take-off, tube, nitrogen gas sparge tube, and heater, 1,4-butanediol (3225 g. = 35.8 moles), ethylene glycol (2226 g. = 35.8 moles) and adipic acid(9549 g. = 65.4 moles) were added. The reaction mixture was gradually heated to 170°–180° Centigrade with the water of reaction being removed continually. When the rate of water removal slowed down, the reaction temperature was increased to 225° ±5° Centigrade and vacuum was slowly and carefully applied until a vacuum of 10 mm Hg was reached. The reaction was stopped when the polyester mixture had an acid number of 17.50. The polyester was stored and used as a master batch for investigation of the catalytic effect of various compounds on the acid numbers of this polyester in Examples 28–36.

The polyester, 1160 grams, was transferred to a two-liter, round bottom reaction flask, equipped with stirrer, thermometer, vacuum pump, condenser, nitrogen gas sparge tube and heater. The polyester was then heated to 225° ±5° Centigrade and a sample removed to determine the initial acid number. The indicated compound was then added and the polyester mixture was allowed to react for one hour. The acid number was checked and additional compound added as indicated. The mixture was then reacted for an additional hour and the final acid number was then determined.

The results in Table III illustrate that the complexes are considerably more reactive than the individual compounds as indicated by the concentration of compound required to achieve the final acid number. The variations in the initial acid number are due to a variation in the time of heating the individual polyester mixture prior to addition of the various compounds.

Table III

| | Examples | | | | | | | | |
|---|---|---|---|---|---|---|---|---|---|
| | 28 | 29 | 30 | 31 | 32 | 33 | 34 | 35 | 36 |
| Compound | B | C | C/2B | A | D | D/A | D/2A | D/3A | D/4A |
| Initial Acid Number | 15.12 | 15.46 | 14.27 | 15.72 | 17.06 | 14.27 | 13.14 | 12.95 | 12.37 |
| Amount of Compound 1st Addition, gms. | 0.03 | 0.03 | 0.03 | 0.03 | 0.03 | 0.03 | 0.03 | 0.03 | 0.03 |
| Acid Number after 1 hour | 9.68 | 1.17 | 3.16 | 9.3 | 0.97 | 4.03 | 3.47 | 5.04 | 5.53 |
| Amount of Compound 2nd Addition, gms. | 0.03 | 0.03 | 0.03 | 0.03 | 0.03 | 0.03 | 0.03 | 0.03 | 0.03 |
| Acid Number after 2 hours | 5.79 | 0.29 | 0.35 | 3.38 | 0.26 | 0.48 | 0.33 | 0.98 | 2.10 |
| (Total Moles of Compound, 1000 gms. of Ester) × 10⁻⁴ | 1.4 | 1.5 | 0.5 | 0.8 | 1.8 | 0.6 | 0.3 | 0.2 | 0.2 |

EXAMPLES 37–39

A branched polyester was prepared by charging a 5-liter four necked, round bottom flask, equipped with a stirrer, thermometer, glass helix packed column, vacuum take-off tube, condenser, nitrogen gas sparge tube and heater with 1440 grams (7.42 moles) of tetraethylene glycol, 995 grams (7.42 moles) of trimethylolpropane and 1083 grams (7.42 moles) of adipic acid. The mixture was heated to 170°–180° Centigrade with constant water removal. As the rate of water removal slowed, the reaction temperature was increased to 225° ±5° Centigrade and a vacuum of 10 millimeters mercury pressure was applied. The reaction was stopped when the polyester mixture reached an acid number of 13.25. The polyester was stored and used as a master batch to determine the catalytic effect of the compounds listed in Table IV below. The indicated quantity of polyester was transferred to a 2-liter round bottom reaction flask, equipped with stirrer, thermometer, glass helix packed column, vacuum take-off tube, condenser, nitrogen gas sparge tube and heater. The polyester was heated to 225° ±5° Centigrade and a sample was removed to determine the initial acid number. The indicated compound was added and the mixture was allowed to react for 1 hour. The acid number was checked and additional compound was added as indicated. These steps were repeated until an acid number of less than 1.0 was obtained. The minor variations in the initial acid number are due to variations in the time of heating the individual polyester samples prior to the compound addition. The results in Table IV illustrate that the complex is more reactive as a catalyst than the individual components as indicated by the reaction time and the concentration of compound required to achieve an acid number of less than 1.

Table IV

| | Examples | | |
|---|---|---|---|
| | 37 | 38 | 39 |
| Weight of Polyester, gms. | 700 | 1160 | 1160 |
| Compound | — | D/2F | F |
| Initial Acid Number | 12.97 | 12.32 | 12.93 |
| 1st Compound Addition, gms. | — | 0.03 | 0.03 |
| Acid Number after 1 hr. | 9.45 | 6.39 | 7.37 |
| 2nd Compound Addition, gms. | — | 0.03 | 0.03 |
| Acid Number after 2 hrs. | 7.39 | 5.30 | 5.27 |

Table IV-continued

| | Examples | | |
|---|---|---|---|
| | 37 | 38 | 39 |
| 3rd Compound Addition, gms. | — | 0.03 | 0.03 |
| Acid Number after 3 hrs. | 6.02 | 2.04 | 3.02 |
| 4th Compound Addition, gms. | — | 0.03 | 0.03 |
| Acid Number after 4 hrs. | 4.44 | 0.48 | 0.94 |
| 5th Compound Addition, gms. | — | — | 0.03 |
| Acid Number after 5 hrs. | 3.68 | — | 0.58 |
| Acid Number after 8 hrs. | 0.46 | — | — |
| (Total Moles of Compound per 1000 gms. of Polyester) $\times 10^{-4}$ | — | 0.6 | 1.8 |

EXAMPLES 40–47

The products of Examples 40–47 were prepared in a one-liter, three-necked flask equipped with a condenser, thermometer, glass helix packed column, nitrogen gas sparge tube, stirrer and Dean-Stark tube. The flask was charged with 390 grams of 2-ethyl hexanol (3 moles), 148 grams of phthalic anhydride (1 mole), and 2 grams of the compound as designated below. The reaction was conducted at a temperature of 200° ±5° Centigrade. The extent of the reaction was determined by measuring the water collected in the Dean-Stark tube. The results of Examples 40–47 in Table V illustrate that the tin-titanium complexes are more efficient catalysts than either compound alone in the preparation of these diesters.

Table V

| Example No. | Compound | (Moles) Compound/ 1000 gms. Ester) $\times 10^{-4}$ | Time Required for 100% Reaction, min. |
|---|---|---|---|
| 40 | A | 81 | 533 |
| 41 | E | 99 | 425 |
| 42 | G | 86 | 340 |
| 43 | C | 150 | 192 |
| 44 | D | 181 | 175 |
| 45 | C/2E | 37 | 140 |
| 46 | D/2A | 33 | 150 |
| 47 | C/2G | 33 | 95 |

The embodiments of the invention in which an exclusive property or privilege is claimed are defined as follows:

1. The method of preparing a complex which comprises mixing a quadrivalent organotitanium compound having the formula $Ti(OR)_4$ wherein R is a radical selected from the group consisting of an aliphatic radical having from 1 to 18 carbon atoms, an alicyclic radical having between 1 and 3 rings, between 5 and 6 carbon atoms per ring and between 5 and 18 carbon atoms per molecule, and an aromatic radical having between 1 and 3 rings and between 6 and 18 carbon atoms per molecule with a quadrivalent organotin compound having the formula:

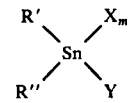

wherein R' and R" are individually alkyl, aryl, alicyclic groups, containing 1 to 18 carbon atoms and may be the same or different, X is an alkyl, aryl, alicyclic, heterocyclic, alkoxyl or carboxyl group having 1 to 18 carbon atoms, Y is an alkoxyl or carboxyl group each containing from 1 to 18 carbon atoms, an oxy or ether group or a group represented by the following formula:

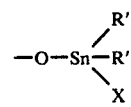

provided that when Y is this group, X is an alkyl group, m is equal to 1 except when Y is an oxy group then m is equal to 0, in a mole ratio from about 1:1 to about 1:4 titanium to tin compound and stirring the mixture until substantially all the titanium compound has reacted with the tin compound to form said complex.

2. The method of claim 1 wherein the organotitanium compound is selected from the group consisting of tetraisopropyl titanate and tetrabutyl titanate and mixtures thereof.

3. The method of claim 1 wherein the organotin compound is selected from the group consisting of dibutyltin diacetate, dibutyltin dilaurate, dibutyltin di(2-ethylhexoate), dioctyltin dilaurate and bis(tributyltin) oxide.

4. The method of claim 1 wherein the mole ratio of organotitanium compound to organotin compound is from about 1:1 to about 1:2.

5. The composition produced by the method as claimed by claim 1.

6. The composition produced by the method as claimed by claim 2.

7. The composition produced by the method as claimed by claim 3.

8. The method as claimed by claim 1 wherein the reaction is conducted in the presence of an inert solvent.

* * * * *